United States Patent [19]
Grey et al.

[11] Patent Number: 5,157,261
[45] Date of Patent: Oct. 20, 1992

[54] DETECTION DEVICE FOR HIGH EXPLOSIVES

[75] Inventors: Alan E. Grey; Judy K. Partin; Mark L. Stone, all of Idaho Falls; Ray M. Von Wandruszka, Moscow; William K. Reagen, Idaho Falls; Jani C. Ingram, Idaho Falls; Gregory D. Lancaster, Idaho Falls, all of Id.

[73] Assignee: EG&G Idaho, Inc., Idaho Falls, Id.

[21] Appl. No.: 707,414

[22] Filed: May 28, 1991

Related U.S. Application Data

[63] Continuation-in-part of Ser. No. 564,239, Aug. 8, 1990, abandoned.

[51] Int. Cl.⁵ ............................................. G01N 21/64
[52] U.S. Cl. ................................... 250/458.1; 385/12; 436/106; 250/227.18
[58] Field of Search ..................... 436/106; 250/458.1, 250/227.14, 227.18; 356/317, 318, 417; 385/12; 422/82.07, 82.08

[56] References Cited

U.S. PATENT DOCUMENTS

| | | | |
|---|---|---|---|
| 4,108,604 | 8/1978 | Heller | 436/106 |
| 4,834,496 | 5/1989 | Blyler, Jr. et al. | 250/227.18 |
| 4,834,497 | 5/1989 | Angel | 385/12 |

*Primary Examiner*—Carolyn E. Fields

[57] ABSTRACT

A portable fiber optic detector that senses the presence of specific target chemicals by electrostatically attracting the target chemical to an aromatic compound coating on an optical fiber. Attaching the target chemical to the coated fiber reduces the fluorescence so that a photon sensing detector records the reduced light level and activates an appropriate alarm or indicator.

12 Claims, 3 Drawing Sheets

DETECTION DEVICE FOR HIGH EXPLOSIVES

CONTRACTUAL ORIGIN OF THE INVENTION

The U.S. Government has rights in this invention pursuant to Contract No. DE-AC07-76IDO1570 between the U.S. Department of Energy and EG&G Idaho, Inc.

This application is a continuation-in-part of application Ser. No. 07/564,239 filed Aug. 8, 1990, and titled "DETECTION DEVICE FOR HIGH EXPLOSIVES" by Grey, et al., now abandoned.

BACKGROUND OF THE INVENTION

This invention relates to a compact and portable detection device for nitrogen base explosive chemical compounds, such as TNT. The portable device can be conveniently carried by an individual, is extremely sensitive to the class of compounds being detected, and is minimally affected by potential interfering substances.

The device of the present invention is based upon the use of fiber optic spectroscopy. Sensors to detect light emitted from an optical fiber can be constructed that are sensitive, compact, readily portable, and require a minimum of training for their use. The preferred process of the invention relies upon a chemical system, and optical and electronic components to monitor a decrease in fluorescence when a subject molecule (such as TNT) interacts with fluorescent polycyclic aromatic Fluorescence is a process by which an atom or molecule emits radiation as a result of the absorption of radiation from another source. In most cases, the transmitted longer wavelength than the absorbed radiation. In the case of most organic molecules, both the absorption and emission radiation wavelengths are in the ultra-violet to visible regions of the spectrum. A variety of materials exhibit fluorescent properties. Some examples of these include fluorescent crystals such as zinc or cadmium sulfide are used in lamp tubes, television screens, scintillation counters, and similar devices. Fluorescent dyes are used for labeling molecules in biochemical research.

Current explosive detection methods utilize neutron beams and energy detection to characterize the organic compounds under surveillance. U.S. Pat. No. 4,882,121, issued Nov. 21, 1989, discloses a neutron generator for supplying neutrons to an object which may to contain an explosive, and a germanium detector and analysis means coupled to the detector which is able to analyze the fast gamma photons emitted by the object and trapped by the detector. The system then determines the nitrogen/oxygen ratio in the object, so that this ratio can be compared with that of the explosive and establish whether the object contains the explosive. A second patent, U.S. Pat. No. 3,997,787, issued Dec. 14, 1976, discloses an apparatus and method for detecting the presence of nitrogen and oxygen-containing explosives within a container by irradiating the container with thermal and high-energy neutrons, and then measuring the quantity of thermal energy neutrons passing through the container and the quantity of radioactive nitrogen 16 generated within the container. The measurements of neutron absorption and nitrogen 16 are correlated to provide an output signal indicative of whether the material within the container is an explosive. A third patent, U.S. Pat. No. 3,146,349, issued Aug. 25, 1964, discloses a method for detecting explosives in luggage in which the explosives have been seeded with a high cross-section neutron absorber by placing a low level thermal neutron source along one side of the luggage. The source having a sufficiently low flux density as to be non-destructive to the contents of ordinary luggage including photographic film, irradiates the luggage with thermal neutrons. By placing a gamma ray detector on the other side of the luggage and comparing the amount of gamma rays emitted directly by the absorber with background gamma rays, it provides an indication of the presence of an explosive.

Although the above devices may be effective, they are too massive, non-portable, and, because of the neutron and gamma radiation, cannot be used near humans without effective shielding, i.e., lead, water or polyethylene.

Dogs can also be trained to sniff out explosives, but the drawbacks are that they require a trainer/handler and have a limited attention span.

The present invention provides a simpler, less expensive, portable device that can be used virtually anywhere including close proximity to humans.

SUMMARY OF THE INVENTION

In its most basic embodiment, the present invention functions by affixing a fluorescent PAH compound at the distal end of an optical fiber or waveguide. When the distal end is exposed to an air sample, a decrease in fluorescence intensity indicates the presence of the explosive compounds in the air sample.

The concept takes advantage of the interaction of high explosives with PAH's. A consequence of this interaction is a change of the fluorescent behavior of the PAH resulting in a decrease, or quenching, of the fluorescent intensity. Thus, sensing of a high explosive is achieved by affixing a PAH to the distal end of the optical fiber, exciting the PAH by means of radiation guided by the optical fiber, and transporting the high explosive vapors over the distal end of the fiber. As a result of the interaction of the high explosive with the PAH, the fluorescent intensity of the PAH is reduced. The fluorescent intensity is monitored by a spectrometer.

The distal end of the fiber is pretreated by removing both the outer, protective jacket and the cladding leaving the core; henceforth, this pretreatment shall be referred to as unjacketing the fiber. As a result of this pretreatment, only the core of the optical fiber is utilized as part of the chemical sensor (also referred to as the distal end). The preferred optical fibers utilized by the invention are multi-mode with 200 micrometers to 1 millimeter diameters.

The fluorescent spectra has been determined for a series of polynuclear aromatic compounds to determine which compound produces the most resolved spectrum. Among others, fluorescent spectrum has been determined for pyrene, anthracene phenanthrene, and perylene. Perylene is preferred for several reasons: the excitation wavelength is 411 nanometer (nm) and there are a well resolved fluorescent peaks at approximately 445 nm and 470 nm. This excitation wavelength being in the visual range simplifies the light source requirements.

The chemical structure of Perylene is shown below.

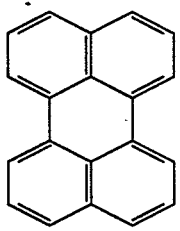

Although PAH's have relatively low vapor pressures, it is still necessary to stabilize the fluorescent molecules on the optical fibers through chemical attachment (i.e., covalent or ionic bonding of a derivatized PAH, encapsulation or entrapment of a PAH). For example, perylene can be chemically attached to the optical fiber by silanating the fiber with 3-aminopropyl trimethoxysilane, and sulfonating the Perylene to obtain either the mono- or di-sulfonate derivative. The sulfonated derivative will then react with the terminal amine group on the silanated fiber and be chemically attached. These reactions are as follows:

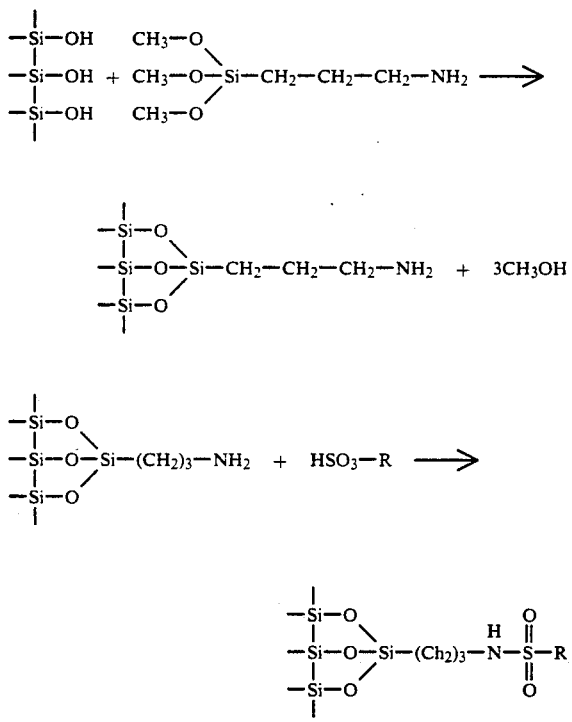

Where R is the polynuclear aromatic compound.

In a preferred optical fiber coating system, there are three components: a (PAH); a hydrocarbon solvent; and a polymer, hereafter referred to as the PAH coating. It is believed that both the selection of polymer and hydrocarbon solvent (e.g., octane, hexadecane, dodecane, triacontane, and qualane) components and their combinations are critical in the formation of stable coatings of encapsulated PAH compounds.

To date, primarily perylene/hydrocarbon solvent-/polymer fiber coatings have been investigated. This work involves the preparation and fluorescence quenching testing of optical fiber coatings (encapsulating matrices for perylene) prepared from combinations of a variety of polymers and solvents. The polymers investigated are listed in the groups below:

| BEST UTILITY | LESSER UTILITY | NO UTILITY |
|---|---|---|
| Polyethylene | Polyethylene oxide | Polystyrene |
| Polymethylpentene | Polypropylene | Polycarbonate |
| | Polyisoprene | bisphenol A |
| | Polybutadiene | Polyvinyl chloride |
| | | Polyacrylic acid |

The solvents investigated listed in order of decreasing utility are: the linear and branched hydrocarbons, aromatic hydrocarbons, and ethers. The preferred encapsulated PAH coating consists of a combination of perylene, squalane ($C_{30}H_{62}$) and polyethylene.

A preferred method of affixing the PAH, in general, to the optical fiber is to add a PAH to a linear or branched chain saturated or unsaturated polymer, such as polyethylene, polypropylene, polybutadiene, or polymethylpentene, that has been dissolved in a high boiling solvent, such as octane, dodecane, hexadecane, squalane, or triacontane. Dipping the fiber into this heated or gelled solution produces a thin, stable polymer coating containing the PAH.

The concentration of the PAH compound on the optical fiber is critical. If the concentration is too high, agglomeration of the molecules occurs and the fluorescent spectrum exhibits broadened peaks. In addition, the high intensity fluorescence saturates the detector which inhibits observing any spectral changes. If the PAH concentration is too low, the fluorescent intensity is week and the signal-to-noise ratio limits detection. As a result, any small incremental change due to quenching would also be too small. The optimum concentration has been experimentally determined.

The apparatus, as currently configured, can detect TNT at a calculated concentration of less than 5 parts per billion (ppb). The concentration of TNT vapor in air was calculated using the work of Dionne, et al., who used an Arrhenius plot with the Clausius-Clapeyron equation to calculate the TNT vapor pressure. The system can readily detect TNT in the pure form and when present in explosive mixtures. Two mixtures were tested: Petalite, which is a mixture of pentaerythritol tetranitrate (PETN) and trinitrotoluene (TNT), and Compound B, which is a mixture of cyclonite (RDX) and TNT.

Explosive mixtures can be made in the form of plastic explosives, which are made of an explosive chemical usually bound in a polymer matrix. Their main advantage is that they can be molded or cast into any desired shape or size. The explosive chemical is typically RDX, HMX, or PETN. The chemical structures of RDX, TNT, HMX, and PETN are shown below.

RDX (Cyclonite)
Cyclo-1,3,5-Trimethylene-2,4,6-Trinitramine

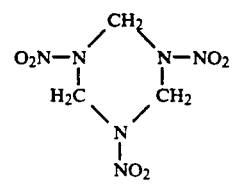

TNT
Trinitrotoluene

-continued

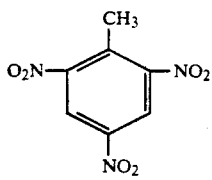

HMX (Octogen)
Cyclotetramethylene Tetranitramine

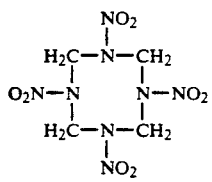

PETN
Pentaerythritol Tetranitrate

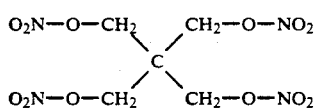

The vapor pressures at ambient temperatures of the above explosive mixtures are estimated as follows:

```
RDX   3.9 × 10⁻⁹   Torr
HMX   1.0 × 10⁻¹⁴  Torr
PETN  5.0 × 10⁻⁹   Torr
```

Therefore, with the exception of HMX, the vapor concentration would be in the parts per trillion (ppt) range. Such concentrations are below the reliable detection limit of most analytical instrumentation. In the process of the present invention, this is overcome by installing a vacuum system to draw a large volume of air over the optical fiber and accumulate analytes to be detected. The optical fiber, in turn, acts as a concentrator, in the same manner as glass tubing or a filter. This technique brings the explosive vapor concentration into the detection range of the inventive apparatus.

Although, as stated above, the present apparatus detected explosives in concentrations of approximately 5 ppb, it is estimated that two orders of magnitude improvement are possible which would lower the detection range to 50 parts per trillion (ppt). This improvement can be accomplished by optimizing:

1. geometry of detector fiber to air flow profile;
2. the detector fiber coating component concentrations
3. the air flow rates;
4. the geometry of the detector and integrating sphere containing the detector; and
5. detector fiber surface area.

In order to detect the attachment of the explosive molecule to the polynuclear compound., optical and electrical components are used to detect a decrease in fluorescence. The balance of the optical fiber is used as a light pipe to transmit light, filtered to the excitation wavelength, to the distal end where the PAH compound is attached. In practice, the fluorescing PAH coated fiber is exposed to an airborne sample containing the explosive to be detected. If the explosive is present, the airborne explosive molecules interact with the fiber, resulting in a decrease in the fluorescent signal. The extent of the decrease is proportional to the concentration of explosive molecules in the surrounding environment.

DETAILED DESCRIPTION OF THE INVENTION

Figure 1:
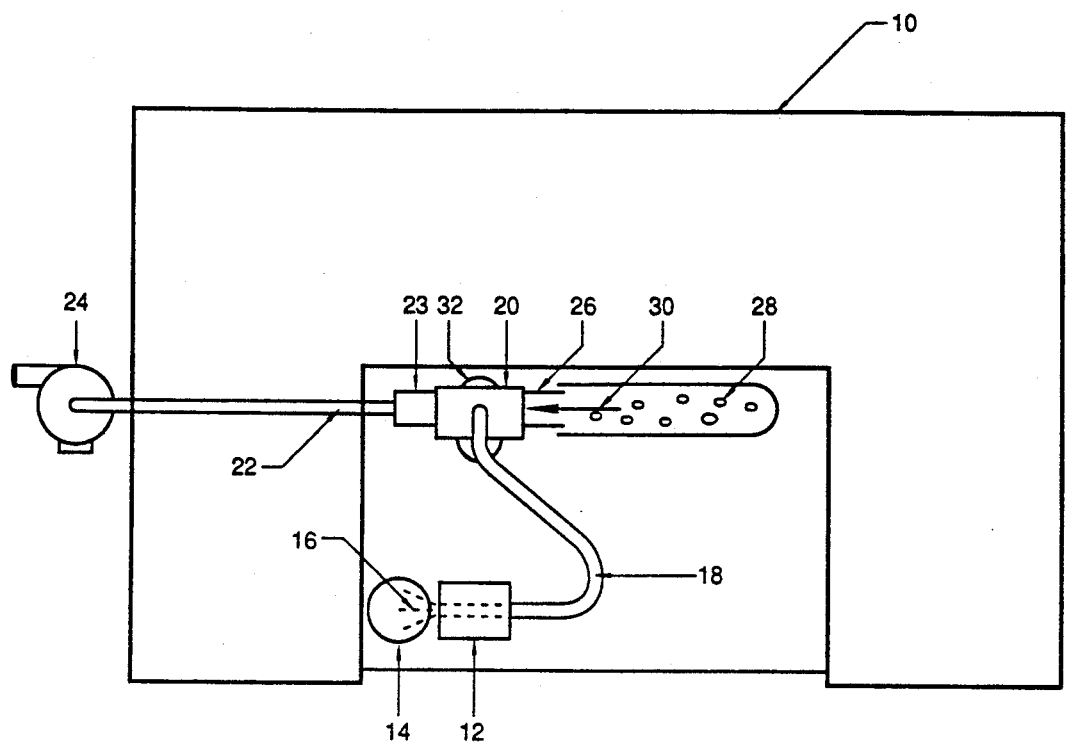
FIG. 1 is a top view schematic representation of a modified fluorimeter useful in the present invention.

The process of the present invention has been confirmed using both a Perkin-Elmer Model 512 Fluorometer and a Photon Technology International (PTI) Alphascan Fluorometer. In FIG. 1, modifications of the Perkin-Elmer instrument for investigation of the chemical sensor optical fibers are shown. (Similar modifications were also employed in the PTI instrument). The fluorometer 10 can be modified with means 12 to position the optical fiber 18 in front of a focusing lens 14 to focus the input beam 16 through fiber 18. The fiber 18 provides the optical path to transmit the light to an end of the fiber coated with a stable coating containing a PAH. A chamber 20 positions the coated end of the fiber 18 in front of the detector as described below. At least two ports are machined into the holder 20 on either side of the optical fiber 18. A first port 23 is affixed through conduit 22 to a vacuum pump 24 to pull sample air over the fiber. A second port 26 permits the sample air containing explosive molecules 28 to enter the chamber 20 as at 30 and contact the Perylene-coated fiber.

Airborne explosive compound molecules 28 pass over the coated exposed tip of fiber 18 and interact with the fiber. This reduces the fluorescent intensity within chamber 20. Light intensity is monitored by a spectrometer through window 32.

Figure 2:
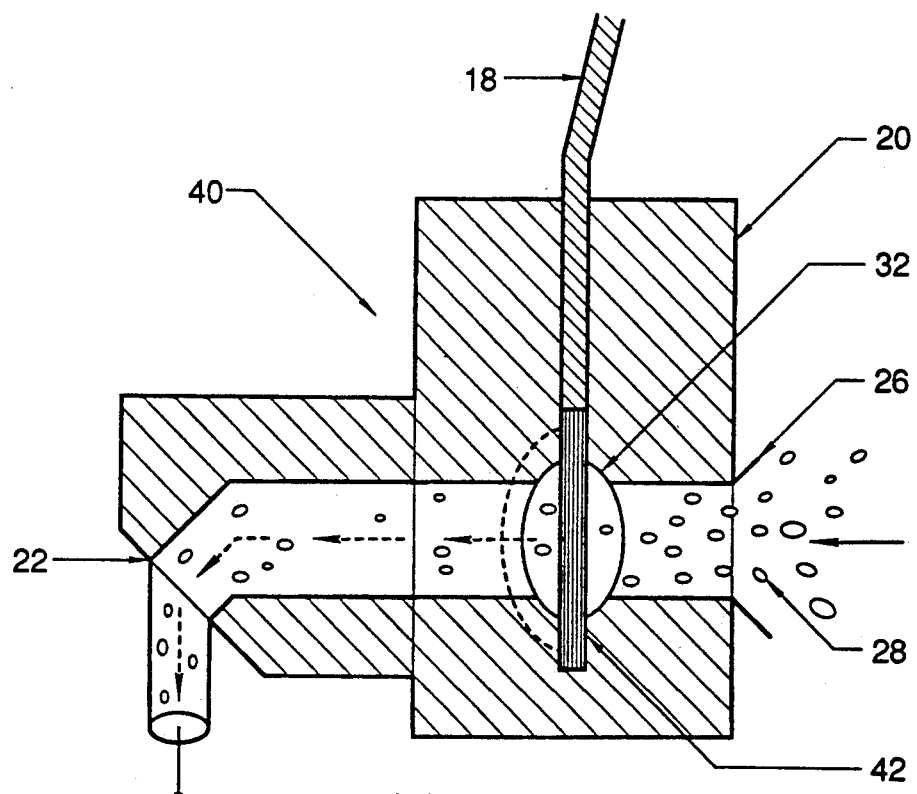
FIG. 2 is a schematic detail of the sensor portion of the fluorometer.

Referring now to FIG. 2, the enlarged sensor assembly 40 comprises a coated distal tip portion 42 of optical fiber 18. While the length of this distal tip portion 42 depends upon the particular devise utilized, the preferred length used by applicants is about one to two centimeters. While the fiber is conventionally jacketed, the distal tip portion 42 is unjacketed to the core and treated to form a chemical sensor. A reactive chemical such as 3-aminopropyltrimethoxysilane can be used as an adhesion promotor that bonds derivatized PAH's (i.e. sulfonated perylene) to the optical fiber. A preferred method of bonding the PAH's to the optical fiber is through an entrapment mechanism. A polymer/solvent mixture is used to solubilize and entrap PAH compounds, then used as a coating on the optical fiber to form the chemical sensor.

The fluorescence of the Chemical Sensor is excited by light transmitted through the fiber and subsequently detected by light monitoring means, such as a spectrometer, through window 32, as in FIG. 2. When the particular explosive molecules enter the chamber 20, the airborne explosive molecules interact with the PAH and reduce the fluorescence. The reduced fluorescence on the tip 42 is detected by the light sensing means. The relative decrease in fluorescence can be extrapolated into a relative quantity of explosive mixture molecules in the airstream directed through chamber 20.

Figure 3:
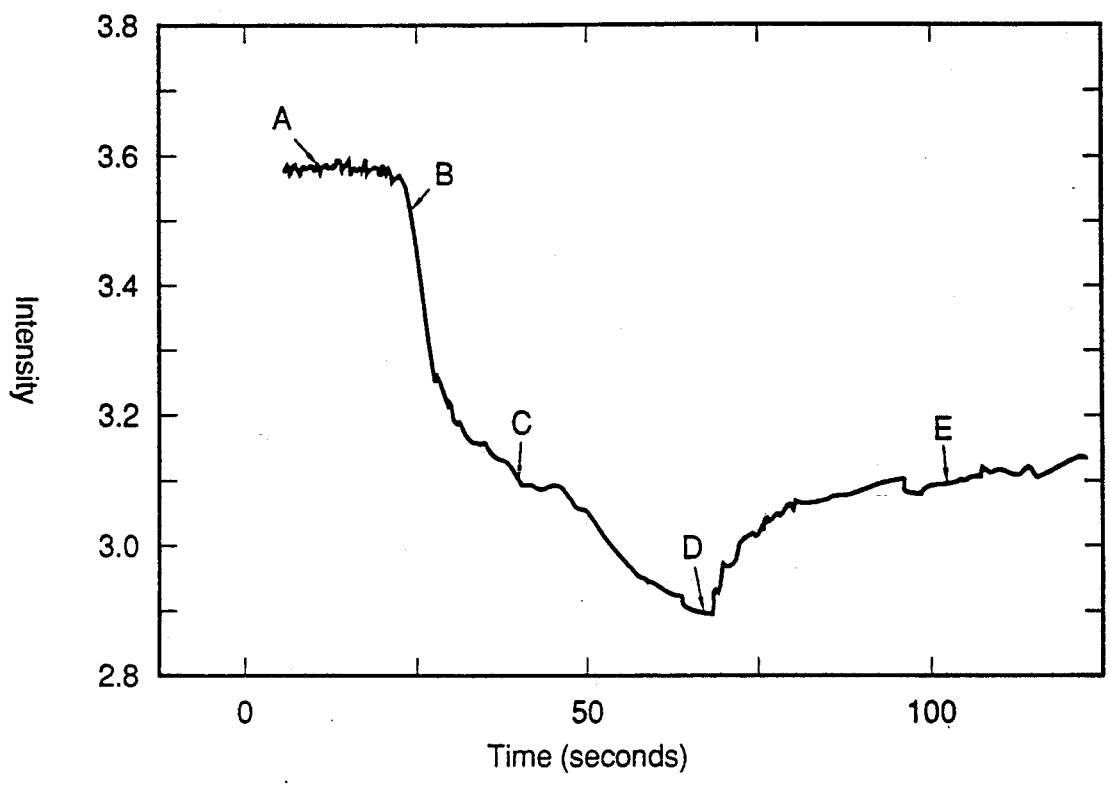
FIG. 3 is a graph of fluorescent intensity of Perylene versus exposure time.

In FIG. 3, a quenching plot of the chemical sensor optical fiber due TO TNT exposure is shown. In this plot, the fluorescent intensity of the encapsulated PAH coating is plotted as a function of time. A baseline fluorescent intensity is established in the region indicated by A. At point B, the sensor is exposed TO TNT vapor. In the region indicated by C, the fluorescent intensity decreases as a result of interaction of the TNT with the encapsulated PAH coating. At point D, TNT exposure to the sensor is terminated. In the region indicated by E, the fluorescent intensity increases due to the desorption of TNT from the encapsulated PAH coating.

Figure 4:
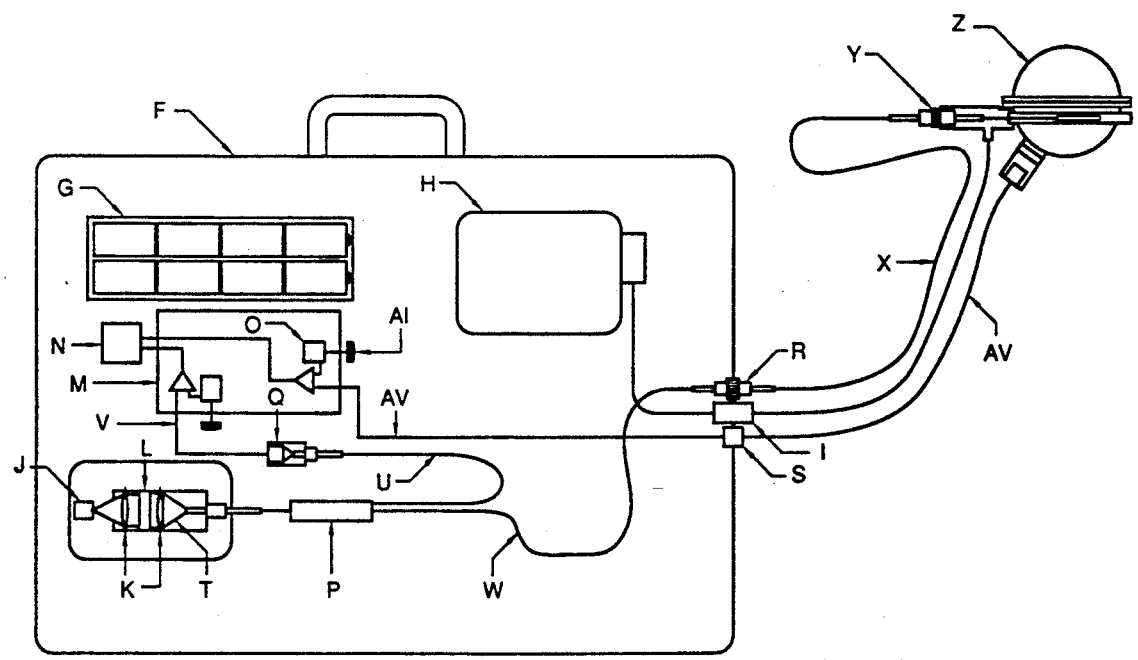
FIG. 4 is a schematic view of the apparatus of the present invention.
Figure 5:
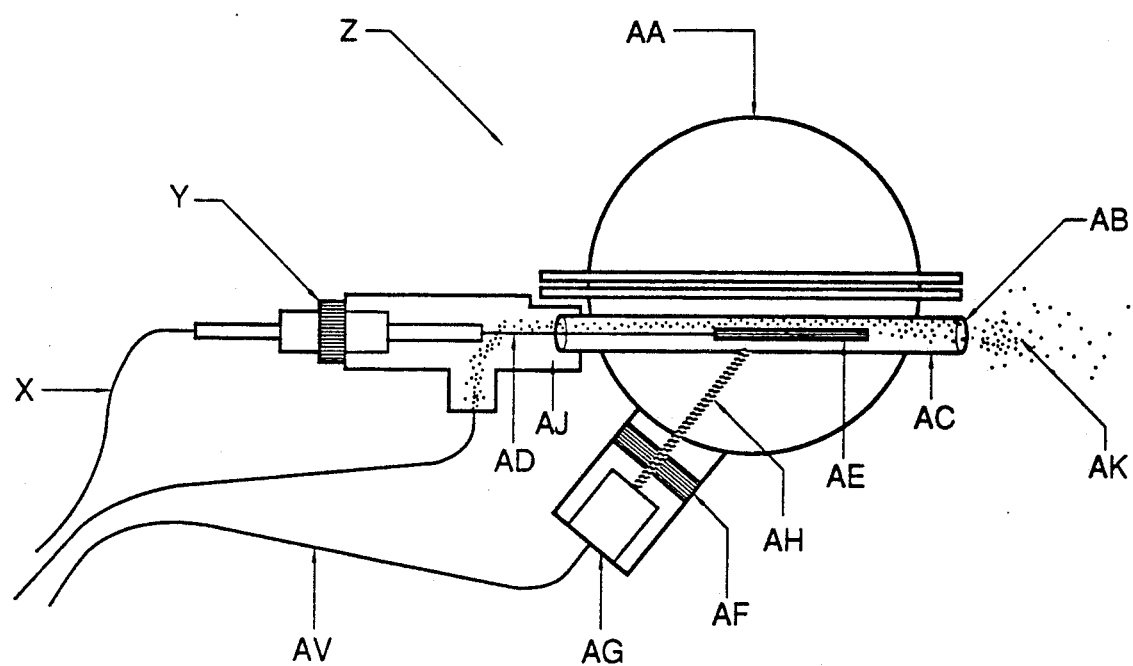
FIG. 5 is a schematic section view of the sensor head.

A preferred embodiment of the apparatus of the present invention is illustrated in FIGS. 4 and 5. Referring to FIG. 4, the apparatus is housed in case F and contains power supply G, vacuum pump H, vacuum connection I, 3.5 watt Krypton lamp J, 18 millimeter focal length lenses K, 10 nanometer optical band pass filter L, electronics assembly M, alarm assembly N, reference voltage O, 90:10 fiber optical beam splitter P, reference photodiode Q, fiber optic feed-through R, and electrical feed-through S. Spectrally filtered light T is focused onto the input of fiber optic beam splitter P. The 10% output of the fiber optic beam splitter U is connected to reference photodiode Q, electrical conductors V, and the electronics assembly M. The 90% output of the fiber optic beam splitter W is connected to fiber optic feed-through R, fiber optic cable X, and fiber optic feed-through Y at sensor assembly Z.

A commercially available vacuum system is used to draw air over the detector fiber. The vacuum pump H chosen has a flow rate variable from one to five liters of air per minute. This unit has its own battery and can operate continuously for ten hours before the battery must be recharged.

The electronics assembly M is comprised of two sub-assemblies, a battery pack G, and an electronic circuit board. This battery pack G contains eight 1.2 volt rechargeable batteries, allowing the unit to operate continuously for approximately four hours before the batteries must be recharged.

The electronic package provides three basic functions: low voltage detection, low light detection, and signal detection. The unit provides both audible and visual alarms at N to alert the operator when an explosive substance is detected.

Referring to FIG. 5, the sensor assembly Z comprises an internally reflective integrating sphere AA, air entry aperture AB, glass tube AC, optical fiber AD with chemical sensor AE, optical bad pass filter AF, and sensor photodiode AG. In operation, Krypton lamp J (FIG. 4) is used to excite chemical sensor optical fiber AE. Optical emission AH of chemical sensor optical fiber AE is transmitted through optical band pass filter AF and onto sensor photodiode AG. Sensor photodiode AG converts the optical signal AH into an electrical signal that passes through electrical conductors AV to electronics assembly M (FIG. 4). The operator sets the reference voltage O with the detector sensitivity adjustment AI. The electronics assembly continuously compares the reference voltage and the sensor photodiode electrical signal. If the sensor photodiode electrical signal at AV decreases below the reference voltage level at O, the alarm assembly will be activated.

During operation, the vacuum pump H is activated, thereby drawing air to be sampled into entry aperture AB of integrating sphere AA to depart the sphere at exit aperture AJ. The air sample passes through glass tube AC and contacts chemical sensor optical fiber AE. If explosive molecules AK are present, they will react with chemical sensor optical fiber AE, thereby reducing the optical emission AH. Reduced light detected by sensor photodiode AG is translated into a reduced electrical output via AV into electronics assembly M. The alarm assembly N will be activated if the electrical signal from sensor photodiode AG is reduced below the precalibrated reference voltage level O determined by the detector sensitivity adjustment AI. The sensor fibers AD and AE may be attached to fiber X via a fiber optic connector Y which permits rapid replacement of the sensor portion of the fiber.

Examples of further experimental data on preparation of the fiber coating consisted of dissolving 150 mg of the polymer (e.g. polyethylene) in 10 ml of solvent (e.g. squalane) then adding the perylene at 125° C. with stirring. Etched optical fibers are then dipped to a depth of about 2 cm in the gelled or hot liquid solution to form the coating.

An example of the fluorescence studies consist of recording a fluorescence spectrum (430-550 nm) prior to each quenching study using an activation wavelength of 411 nm. The quenching of perylene fluorescence is effected by exposing fluorescing fibers to TNT vapors. The fibers are typically exposed to TNT vapors for 60-100 sec duration while monitoring the fluorescence intensity at the peak maximum determined from the fluorescence spectrum (between 440-455 nm). Fiber fluorescence is monitored 0.5-1.5 min before and 0.5-1.5 min after the TNT vapor exposure. TNT vapors are drawn through the fiber cell using an air-flow system similar to FIG. 1.

While a preferred embodiment of the invention has been disclosed, various modes of carrying out the principles disclosed herein are contemplated as being within the scope of the following claims. Therefore, it is understood that the scope of the invention is not to be limited except as otherwise set forth in the claims.

We claim:

1. A fiber optic detector apparatus for use in detecting explosive molecular compounds in air, comprising:
   a. a chamber operably connected to a photon sensing device;
   b. a clear tube within the chamber having an entry aperture and an exit aperture;
   c. an optical fiber within said clear tube, at least a portion of said optical fiber at a distal end having affixed thereto a stable coating of a fluorescent polycyclic aromatic compound, said coating comprising: a polymer, a hydrocarbon solvent, and a fluorescing polycyclic aromatic hydrocarbon formulated to interact with the explosive molecular compounds;
   d. air evacuation means connected to the exit aperture;
   e. a filtered light source directing light into the optical fiber; and
   f. an electronic package connected to the photon sensing device comprising power supply and alarm means, such that a change in fluorescent intensity at the optical fiber coating can be detected by the photon sensing device and the alarm means can be activated.

2. The apparatus as recited in claim 1, wherein the photon sensing device comprises a detector photodiode and a band pass filter and the distal tip has a length of about 2 cm.

3. The apparatus as recited in claim 1, wherein the chamber is a sphere having a reflective inner surface.

4. The apparatus as recited in claim 1, wherein said stable coating comprises a mixture of perylene, squalane, and polyethylene.

5. The apparatus as recited in claim 1, wherein the hydrocarbon solvent is selected from the group consisting of octane, hexadecane, dodecane, triacontane, and squalane.

6. The apparatus as recited in claim 1, wherein the polymer is selected from the group consisting of polyethylene, polymethylpentene, polyethylene oxide, polypropylene, polyisoprene, and polybutadiene.

7. The apparatus as recited in claim 1, wherein the flourescing polycyclic aromatic hydrocarbon is perylene.

8. A fiber optic detector apparatus for use in detecting explosive compounds in air, comprising:
   a. A chamber operably connected to a photon sensing device;
   b. A clear tube within the chamber having an entry aperture and an exit aperture;
   c. An optical fiber within said clear tube having a stable coating of a fluorescent polycyclic aromatic compound adhered thereto, said coating being formed of a solution of perylene, a saturated organic polymer and a saturated solvent, such that a change in fluorescence of said optical fiber is produced when in contact with the explosive compounds;
   d. Vacuum means connected to the exit aperture;
   e. a filtered light source directing light into the optical fiber, said filtered light source comprising a krypton lamp, a first lens adjacent the lamp, a band pass filter adjacent the first lens, a second lens adjacent the filter, and a fiber optic beam splitter adjacent the filter; and
   f. an electronic package connected to the photon sensing device comprising power supply and alarm means, such that a change in fluorescence of said optical fiber can be detected by the photon sensing device and the alarm means can be activated.

9. The apparatus as recited in claim 8, wherein the photon sensing device comprises a detector photodiode and a band pass filter.

10. The apparatus as recited in claim 8, wherein the chamber is a sphere having a reflective inner surface.

11. The apparatus as recited in claim 8, wherein the fluorescent compound is selected to interact with explosive compounds selected from the group consisting of TNT and mixtures containing TNT.

12. A method of detecting explosive vapors in air, comprising:
   a. providing an air passageway through a detection chamber;
   b. inserting a chemical sensor optical fiber into the detection chamber, said optical fiber having a chemical coating comprising a combination of perylene, polyethylene, and squalane,
   c. exposing the chemical sensor optical fiber to an air sample containing the explosive vapors;
   d. measuring the fluorescent intensity of the chemical sensor optical fiber; and
   e. comparing the measured fluorescent intensity with a reference level and activating an alarm means if the level of fluorescent intensity decreases below a preset limit as a result of interaction of the explosive vapors with the chemical sensor optical fiber coating;
   f. comparing the measured level of fluorescence with a reference level and setting off alarm means if the level of fluorescence decreases below a preset limit as a result of attachment of a target chemical to the optical fiber coating.

* * * * *